(12) United States Patent
Ding et al.

(10) Patent No.: US 10,780,091 B2
(45) Date of Patent: Sep. 22, 2020

(54) TLR7 AGONIST MALEATE SALT, CRYSTALLINE FORMS C, D AND E THEREOF, PREPARATION METHODS AND USES OF MALEATE SALT AND CRYSTALLINE FORMS

(71) Applicant: CHIA TAI TIANQING PHARMACEUTICAL GROUP CO., LTD., Jiangsu, Lianyungang (CN)

(72) Inventors: Zhaozhong Ding, Shanghai (CN); Fei Sun, Shanghai (CN); Yinghu Hu, Shanghai (CN); Yilong Zhou, Shanghai (CN); Zheng Wang, Shanghai (CN); Ling Yang, Lianyungang (CN)

(73) Assignee: CHIA TAI TIANQING PHARMACEUTICAL GROUP CO., LTD., Jiangsu, Lianyungang (CN)

( * ) Notice: Subject to any disclaimer, the term of this patent is extended or adjusted under 35 U.S.C. 154(b) by 0 days.

(21) Appl. No.: 16/075,080

(22) PCT Filed: Feb. 4, 2017

(86) PCT No.: PCT/CN2017/072890
§ 371 (c)(1),
(2) Date: Aug. 2, 2018

(87) PCT Pub. No.: WO2017/133683
PCT Pub. Date: Aug. 10, 2017

(65) Prior Publication Data
US 2019/0070179 A1 Mar. 7, 2019

(30) Foreign Application Priority Data
Feb. 5, 2016 (CN) .......................... 2016 1 0082030

(51) Int. Cl.
| A61K 31/519 | (2006.01) |
| C07D 487/04 | (2006.01) |
| A61P 31/12  | (2006.01) |
| A61K 31/015 | (2006.01) |

(52) U.S. Cl.
CPC .......... *A61K 31/519* (2013.01); *A61K 31/015* (2013.01); *A61P 31/12* (2018.01); *C07D 487/04* (2013.01)

(58) Field of Classification Search
CPC .................................................. A61K 31/519
USPC ...................................................... 514/256
See application file for complete search history.

(56) References Cited

U.S. PATENT DOCUMENTS

| 6,028,076 A | 2/2000 | Hirota et al. |
| 6,329,381 B1 | 12/2001 | Kurimoto et al. |
| 9,962,388 B2 | 5/2018 | Ding et al. |
| 10,259,814 B2 | 4/2019 | McGowan et al. |

| 2010/0143301 A1 | 6/2010 | Desai et al. |
| 2014/0316132 A1 | 10/2014 | Desai et al. |
| 2015/0266883 A1 | 9/2015 | Coe et al. |
| 2015/0284396 A1 | 10/2015 | Coe et al. |
| 2015/0299204 A1 | 10/2015 | Coe et al. |
| 2017/0273983 A1 | 9/2017 | Ding et al. |
| 2019/0031666 A1 | 1/2019 | Ding et al. |
| 2019/0040071 A1 | 2/2019 | Ding et al. |
| 2019/0040072 A1 | 2/2019 | Ding et al. |

FOREIGN PATENT DOCUMENTS

| CA | 3013518 A1 | 8/2017 |
| CL | 2016002751 A1 | 12/2016 |
| CL | 201801210 | 5/2018 |
| CL | 201801216 | 5/2018 |
| CL | 2018002089 A1 | 12/2018 |
| CN | 104780922 A | 7/2015 |
| CN | 104780923 A | 7/2015 |
| CN | 104780924 A | 7/2015 |
| CN | 104837840 A | 8/2015 |
| CN | 105367576 A | 3/2016 |
| CN | 104780924 B | 9/2016 |
| CN | 104780923 B | 3/2017 |
| CN | 104837840 B | 8/2017 |

(Continued)

OTHER PUBLICATIONS

International Search Report, dated May 10, 2017, issued in corresponding International Application No. PCT/CN2017/072890.

(Continued)

*Primary Examiner* — Taofiq A Solola
(74) *Attorney, Agent, or Firm* — Foley & Lardner LLP

(57) ABSTRACT

The present invention relates to a maleate salt of a compound represented by formula I, a method for preparing the salt, a pharmaceutical composition containing the salt, and the use of the salt. The present invention also relates to crystalline forms C, D and E of the maleate salt of the compound represented by formula I, methods for preparing the crystalline forms, crystalline compositions and pharmaceutical compositions containing the crystalline forms, and uses thereof.

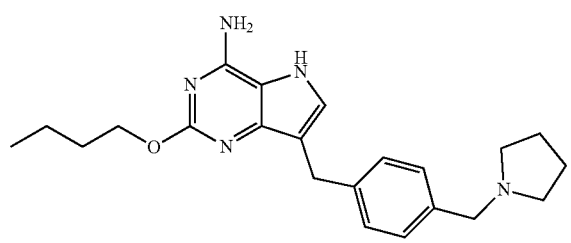

16 Claims, 3 Drawing Sheets

(56) References Cited

FOREIGN PATENT DOCUMENTS

| | | | |
|---|---|---|---|
| EA | 201790389 A1 | 6/2017 | |
| EP | 3 190 113 A1 | 7/2017 | |
| EP | 3 381 918 A1 | 10/2018 | |
| JP | 2009-504803 A | 2/2009 | |
| JP | 2014-504644 A | 2/2014 | |
| WO | WO-2007/024707 A2 | 3/2007 | |
| WO | WO-2009/005687 A1 | 1/2009 | |
| WO | WO-2009/019553 A2 | 2/2009 | |
| WO | WO-2010/077613 A1 | 7/2010 | |
| WO | WO-2012/106522 A2 | 8/2012 | |
| WO | WO-2014/056953 A1 | 4/2014 | |
| WO | WO-2014/081643 A1 | 5/2014 | |
| WO | WO-2014/081644 A1 | 5/2014 | |
| WO | WO-2014/081645 A1 | 5/2014 | |
| WO | WO-2015/124591 A1 | 8/2015 | |
| WO | WO-2015/168269 A1 | 11/2015 | |
| WO | WO-2015/168279 A1 | 11/2015 | |
| WO | WO-2016/023511 A1 | 2/2016 | |
| WO | WO-2016/107536 A1 | 7/2016 | |
| WO | WO-2017/076346 A1 | 5/2017 | |
| WO | WO-2017/133684 A1 | 8/2017 | |
| WO | WO-2017/133686 A1 | 8/2017 | |
| WO | WO-2017/133687 A1 | 8/2017 | |

OTHER PUBLICATIONS

Chilean Office Action, issued in Chilean Pat. App. No. 201802089, 11 pages (dated Oct. 15, 2019).
Chilean Office Action, issued in Chilean Pat. App. No. 201802089, 14 pages (dated Jun. 17, 2019).
Chinese Office Action, issued in Chinese Pat. App. No. 201780009746. 0, 8 pages (dated Oct. 28, 2019).
Database Registry CAS RN 1392818-28-8 (Aug. 29, 2012).
Eurasian Office Action, issued in Eurasian Pat. App. No. 201891770/ 28, 4 pages (dated Nov. 12, 2019).
European Examination Report, issued in corresponding European Pat. App. No. 17747003.6, 5 pages (dated Dec. 13, 2019).
European Extended Search Report, issued in European Pat. App. No. 17747003.6, 11 pages (dated Jun. 25, 2019).
Greene, et al., "Protective Groups in Organic Synthesis", 2nd Ed., pp. 362-385 (1991).
Hackam, et al., JAMA 296(14): 1731-1732 (2006).
Hoffmann, "The immune response of Drosophila", Nature 426: 33-38 (2003).
Jordan, "Tamoxifen: a Most Unlikely Pioneering Medicine", Nature Reviews 2: 205 (2003).
Kanzler, et al., "Therapeutic targeting of innate immunity with Toll-like receptors agonists and antagonists", Nature Medicine 13(5): 552-559 (2007).
Lanford, et al., "Gs-9620, an Oral Agonist of Toll-Like Receptor-7, Induces Prolonged Suppression of Hepatitis B Virus in Chronically Infected Chimpanzees", Gastroenterology 144: 1508-1517 (2013).
Lima, et al., "Bioisosterism a Useful Strategy for Molecular Modification and Drug Design", Current Medicinal Chemistry 12: 23-49 (2005).
Maehr, "A Proposed New Convention for Graphic Presentation of Molecular Geometry and Topography", Journal of Chemical Education 62(2): 114-120 (1985).
Mahadevan,et al., "A General Method for C3 Reductive Alkylation of Indoles", Tetrahedron Letters 44: 4589-4591 (2003).
Notice Prior to Examination, issued in Israeli Pat. App. No. 260965, 4 pages (dated Oct. 24, 2019).
Otmar, et al., "Synthesis and antiproliferative activity of 2,6-diamino-9-benzyl-9-deazapurine and related compounds", Bioorganic & Medicinal Chemistry 12: 3187-3195 (2004).
Powder XRD, Journal of Visualized Experiments, 3 pages (2017) [Retrieved from https://www.jove.com/science-education/10462].
Remington, the Science and Practice of Pharmacy, 21st Ed., Ch. 39-42, 89 pp. (2005).
Roethle, et al., "Identitication ana Optimization of Rteriainone Toll-like Receptor I (TLR7) Agonists for the Oral Treatment of Viral Hepatitis", J. Med. Chem. 56: 7324-7333 (2013).
Sauder, "Imiquimod: modes of action", British Journal of Dermatology 149 (Suppl. 66): 5-8 (2003).
Singaporean Written Opinion, issued in Singaporean Pat. App. No. 11201806682T, 7 pages (dated Sep. 20, 2019).
Single-Crystal versus Powder Diffraction, 3 pages.
Stout, et al., "X-Ray Structure Determination", 2nd Ed., Ch. 3, 21 pages (1989).
Takeda, et al., "Toll-Like Receptors", Annu. Rev. Immunol. 21: 335-376 (2003).
Ulevitch, "Therapeutics Targeting the Innate Immune System", Nature Reviews—Immunology 4: 512-520 (2004).
Wu, et al., "Resiquimod: a new immune response modifier with potential as a vaccine adjuvant for Th1 immune responses", Antiviral Research 64: 79-83 (2004).
Xix C Chinese Pharmacopoeia, pp. 199-201.
Invitation to File a Translation of a Previous Application, issued in EP Pat. App. No. 17747003.6, 1 page (Jul. 12, 2019).

TLR7 AGONIST MALEATE SALT, CRYSTALLINE FORMS C, D AND E THEREOF, PREPARATION METHODS AND USES OF MALEATE SALT AND CRYSTALLINE FORMS

CROSS-REFERENCE TO RELATED APPLICATIONS

This application is a national phase of International Application No. PCT/CN2017/072890, filed on Feb. 4, 2017, which claims priority to Chinese Patent Application No. 201610082030.0, filed on Feb. 5, 2016, each of which is incorporated herein by reference in its entirety.

TECHNICAL FIELD

The present invention relates to the field of medicinal chemistry, and particularly relates to a maleate of TLR7 agonist, a preparing process thereof, a pharmaceutical composition comprising the same and use thereof. The present invention also relates to crystal form C, crystal form D and crystal form E of the salt, preparing processes, crystalline compositions comprising the crystal forms, pharmaceutical compositions comprising the crystal forms or crystalline compositions and use thereof.

BACKGROUND

Toll-like receptor is expressed by various immune cells and recognizes high reserved structural motifs: Pathogen Associated Molecular Pattern (PAMP) expressed by microorganism pathogens or Damage Associated Molecular Patterns (DAMP) released by dead cells. PAMP or DAMP stimulates Toll-like receptor to trigger signal cascade which induces the activations of transcriptional factors like AP-1, NF-κB and interferon regulators (pulse response function). It results in various cell responses, including productions of interferons, proinflammatory cytokines and effector cytokines, whereby immune response is produced. By far, 13 types of Toll-like receptors have been discovered in mammal. Toll-like receptors 1, 2, 4, 5 and 6 are mainly expressed on the cell surface while Toll-like receptors 3, 7, 8 and 9 are expressed in the endosome. Different Toll-like receptors recognize ligands derived from different pathogens. Toll-like receptor 7 (TLR7) is mainly expressed by plasmaeytoid dendritic cells (pDC), and recognized via ligand to induce the secretion of interferon α (IFN-α). Toll-like receptor 7 (TLR7) and Toll-like receptor 8 (TLR8) are highly homologous and therefore the ligand of TLR7 in most cases is also that of TLR8. TLR8 stimulation mainly induces the productions of cytokines like tumor necrosis factor α (TNF-α) and chemoattractant. Interferon α is one of the medicines for treating chronic hepatitis B or hepatitis C while TNF-α is a proinflammatory cytokine, of which the over secretion will result severe side effects.

There have been reported several TLR7 agonists, like imiquimod (British Journal of Dermatology 2003; 149 (Suppl. 66): 5-8), resiquimod (Antiviral Research 64 (2004) 79-83), GS-9620 (Gastroenterology (2013), 144(7), 1508-1517). Nevertheless, it is desirable to have novel TLR7 agonists with better selectivity, activity and safety.

Chinese Patent Application No. 201410405136.0 which is incorporated in its entirety by reference herein discloses one small molecule, i.e. 2-butoxy-7-(4-(pyrrolidin-1-ylmethyl) benzyl)-5H-pyrrolo[3,2-d]pyrimidin-4-amine and preparing process thereof, which has the following structure:

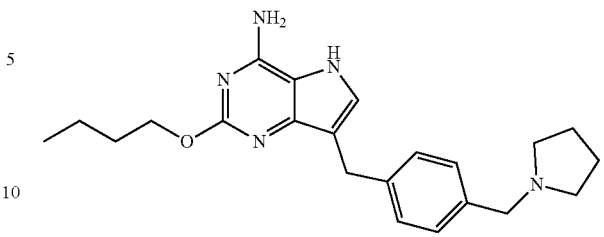

SUMMARY

In an aspect, provided is a maleate of the compound of formula I:

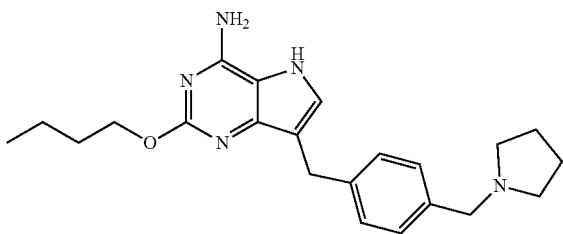

In another aspect, provided are crystal forms of the maleate of the compound of formula 1, the corresponding preparing process and the crystalline composition. In one embodiment, the crystal form is crystal form C, crystal form D or crystal form E.

In one embodiment, the crystal form C is characterized by an X-ray powder diffraction (XRPD) pattern having diffraction peaks at 2θ=7.6°±0.2°, 9.9°±0.2°, 17.8°±0.2°, 22.8°±0.2°, 24.2°±0.2°, 26.3°±0.2°.

In one embodiment, the crystal form D is characterized by an X-ray powder diffraction (XRPD) pattern having diffraction peaks at 2θ=5.1°±0.2°, 9.5°±0.2°, 11.2°±0.2°, 17.6°±0.2°, 20.2°±0.2°, 23.0°±0.2°.

In one embodiment, the crystal form E is characterized by an X-ray powder diffraction (XRPD) pattern having diffraction peaks at 2θ=4.9°±0.2°, 5.3°±0.2°, 9.0°±0.2°, 16.5°±0.2°, 19.3°±0.2°.

In another aspect, provided is a pharmaceutical composition, comprising one or more crystal forms or the crystalline composition thereof according to the invention. The pharmaceutical composition can further optionally comprise pharmaceutically acceptable carrier, excipient and/or medium.

In another aspect, provided is a method for treating or preventing Toll-like receptor 7 (TLR7) associated disease, comprising administering to a subject in need thereof the crystal form or the crystalline composition or the pharmaceutical composition according to the invention in an effective amount. Preferably, the disease is virus infection.

In a further aspect, provided is use of the crystal form or the crystalline composition or the pharmaceutical composition according to the invention for the manufacture of a medicament for treating or preventing Toll-like receptor 7 (TLR7) associated disease. Preferably, the disease is virus infection.

In a yet further aspect, provided is the crystal form or the crystalline composition or the pharmaceutical composition according to the invention for use in treating or preventing Toll-like receptor 7 (TLR7) associated disease. Preferably, the disease is virus infection.

In one embodiment of the invention, the virus infection is hepatitis virus infection, particularly hepatitis B or hepatitis C virus infection.

DETAILED DESCRIPTION

General Definition and Terminology

Figure 1:
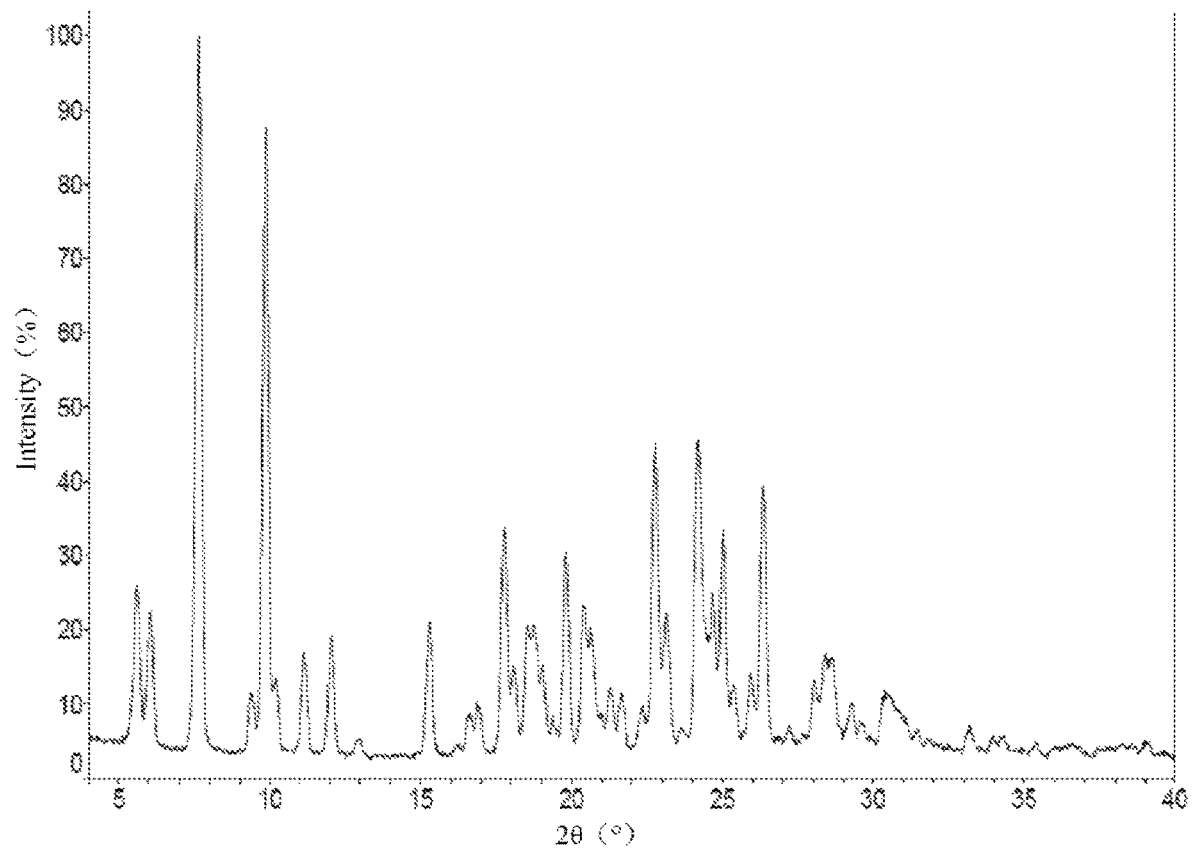
FIG. 1: XRPD pattern of the crystal form C of the maleate of the compound of formula I.

Unless stated otherwise, the terms and phrases used herein have the following meaning. A specific term or phrase shall not be considered as unclear or indefinite when it is not specifically defined. It should be understood according to the general meaning. The trade name used herein refers to the corresponding product or the active ingredient.

Unless specifically defined otherwise, proportion (including percentage) or part is calculated based on weight herein.

When used with a numerical variable, the term "approximate" or "about" usually refers to the value of the variable and all the values of the variable within the experimental error (for example, within an average 95% confidence interval) or within ±10% of the specified value, or a wider range.

The expression "comprise" or its synonyms "contain", "include", "have" or the like is open-ended, which does not exclude other unlisted elements, steps or ingredients. The expression "consist of" excludes any unlisted elements, steps or ingredients. The expression "substantially consist of" refers to specified elements, steps or ingredients within a given range, together with optional elements, steps or components which do not substantively affect the basic and novel feature of the claimed subject matter. It should be understood that the expression "comprise" encompasses the expressions "substantially consist of" and "consist of".

The term "optional" or "optionally" means the event described subsequent thereto may or may not happen. This term encompasses the cases that the event may or may not happen.

The term "pharmaceutical composition" refers to an active ingredient, which is optionally combined with one or more pharmaceutically acceptable components (for example, but not limited to carrier and/or excipient). The active ingredient is exemplified as the compound of formula I or maleate thereof, one or more crystal forms according to the invention, or one or more crystalline compositions according to the invention.

The term "pharmaceutically acceptable carrier" refers to those carriers which have no significant irritation and do not impair the bioactivity and property of the active compound. The "pharmaceutically acceptable carrier" refers to inert substance which is administered with active ingredient and is beneficial to the administration thereof, and comprises but not limited to any of the following substances approved by State Food and Drug Administration for use in human or animal (e.g. livestock): glidant, sweetening agent, diluent, preservative, dye/colorant, flavoring agent, surfactant, wetting agent, dispersant, disintegrant, suspending agent, stabilizing agent, isotonic agent, solvent or emulsifying agent. Non-limiting examples of the carriers comprise calcium carbonate, calcium phosphate, various sugars and starches, cellulose derivative, gelatine, vegetable oil and polyethylene glycol or the like. Other information regarding the carriers may be found in Remington: The Science and Practice of Pharmacy, 21st Ed., Lippincott, Williams & Wilkins (2005), of which the contents are incorporated herein by reference. The term "excipient" generally refers to the carrier, diluent and/or medium used to formulate effective pharmaceutical composition.

The term "administration" or "administrating" or the like refers to a method that enables a compound or composition to be delivered to a desired site of biological action. Such methods comprise but not limited to oral, parenteral (including intravenous, subcutaneous, intraperitoneal, intramuscular, intravascular injection or infusion), local, rectal administration or the like.

As for pharmaceutical or pharmacological active agent, the term "effective amount" refers to the amount of the medicament or agent which is not toxic but sufficient to achieve the desired effect. With respect to the oral formulation herein, the "effective amount" for an active substance in the composition refers to the amount required to achieve the desired effect in combination with another active substance in the composition. The effective amount may be determined individually and depends on the age and general condition of the receptor as well as specific active substance. The effective amount in specific case can be determined by a person skilled in the art through conventional test.

The term "active ingredient", "therapeutic agent", "active substance" or "active agent" refers to a chemical entity useful for treating or preventing target disorder, disease or condition effectively. The term herein may refer to for example the compound of formula I or maleate thereof, one or more crystal forms according to the invention or one or more crystalline compositions according to the invention.

In X-ray powder diffraction (XRPD or XRD) spectra, the diffraction pattern obtained from crystalline compound is generally characteristic for a particular crystal form in which the relative intensities of the bands (especially at low angles) may vary with the dominant orientation effect due to the difference of crystallization conditions, particle diameters, and other measuring conditions. Therefore, the relative intensities of diffraction peaks are not characteristic for the given crystal form. It is more important to note the relative positions of peaks rather than their relative intensities when determining whether the crystal form is the same as that known in the art. In addition, there may be slight errors in the positions of the peaks for any given crystal form, which is also well known in the art of crystallography. For example, the position of the peak may shift due to the change in temperature, sample movement or instrument calibration during analysis of the sample; and the measuring error of $2\theta$ value may sometimes be about ±0.2°, typically about ±0.1°. Therefore, this error should be taken into account when determining the crystal structure. If the crystal forms according to the invention are described as substantially as shown in the figure, the term "substantially" is also intended to encompass such differences in the diffraction peak.

In the XRPD pattern, the peak position is usually represented by angle $2\theta$ or crystal surface distance d and a simple conversion between d and $\theta$ is $d=\lambda/2 \sin \theta$, where d represents the crystal surface distance, $\lambda$ represents the wavelength of the incident X-ray, and θ is diffraction angle. As for the same crystal form of the same compound, the peak positions of the XRPD pattern are similar as a whole, and the relative intensity error may be large. It should also be noted that, in identification of a mixture, some diffraction lines may be lost due to the factors like decrease in content, etc., and thus it is not necessary to rely on the entire bands observed in the high purity sample, and even one band may be characteristic for a given crystal.

Differential scanning calorimetry (DSC) is used to measure the transition temperature when a crystal absorbs or releases heat due to changes in its crystal structure or crystal melting. The thermal transition temperature and the melting point error are typically within about 5° C., usually about 3° C. for the same crystal form of the same compound in a continuous analysis. When a compound is described as having a given DSC peak or melting point, it means the DSC peak or melting point±5° C. Provided is an auxiliary method by DSC to identify different crystal forms. Different crystal forms may be identified according to their different transition temperature characteristics. It is noted that the DSC peak or melting point of the mixture may vary over a wide range. In addition, the melting temperature is associated with the rate of temperature rise due to the decomposition during the melting of the substance.

Differential scanning calorimetry (DSC) herein is measured by the following method: apparatus: TA Q2000 differential scanning calorimeter; method: a sample (~1 mg) is placed in a DSC aluminum pan, method: 25° C.~300° C., heating rate 10° C./min.

The term "crystalline composition" refers to a solid form, which comprises one or more crystal forms according to the invention (such as, crystal form C, D and/or E). The amounts of crystal forms contained in the crystalline composition may be 50% or more, 80% or more, 90% or more, or 95% or more independently. In addition to crystal form according to the invention, the crystalline composition may also optionally comprise other crystal or amorphous form of the compound of formula I or the salt thereof (such as maleate) or the impurities other than these substances. It should be understood by those skilled in the art that the sum of contents of the components in the crystalline composition should be 100%.

Maleate of the Compound of Formula I

Provided is a maleate of the compound of formula I:

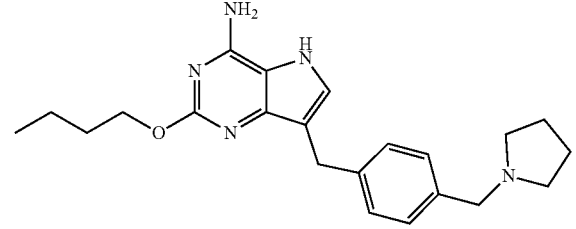

I

In a preferred embodiment, in maleate of the compound of formula I, the molar ratio of the compound of formula I to maleic acid is 1:1~3, preferably 1:2. The maleate of the compound of formula I can be prepared by conventional maleate preparing process.

Crystal Form C

Provided is crystal form C of maleate of the compound of formula I, which has diffraction peaks at 2θ=7.6°±0.2°, 9.9°±0.2°, 17.8°±0.2°, 22.8°±0.2°, 24.2°±0.2°, 26.3°±0.2° in X-ray diffraction (XRPD) pattern.

In a specific embodiment, the crystal form C has diffraction peaks at 2θ=5.6°±0.2°, 7.6°±0.2°, 9.9°±0.2°, 17.8°±0.2°, 19.8°±0.2°, 22.8°±0.2°, 24.2°±0.2°, 25.0°±0.2°, 26.3°±0.2° in X-ray diffraction (XRPD) pattern.

In a more specific embodiment, the crystal form C has diffraction peaks at 2θ=5.6°±0.2°, 6.0°±0.2°, 7.6°±0.2°, 9.9°±0.2°, 12.0°±0.2°, 15.3°±0.2°, 17.8°±0.2°, 18.5°±0.2°, 19.8°±0.2°, 20.4°±0.2°, 22.8°±0.2°, 23.1°±0.2°, 24.2°±0.2°, 24.7°±0.2°, 25.0°±0.2°, 26.3°±0.2° in X-ray diffraction (XRPD) pattern.

In a particular embodiment, diffraction peaks of the crystal form C of the maleate of the compound of formula I are characterized as follows:

| Number | 2θ ± 0.2 (°) | Relative intensity (%) |
|--------|--------------|------------------------|
| 1 | 5.6 | 22.0 |
| 2 | 6.0 | 18.7 |
| 3 | 7.6 | 100.0 |
| 4 | 9.4 | 8.0 |
| 5 | 9.9 | 87.7 |
| 6 | 10.2 | 9.8 |
| 7 | 11.1 | 13.8 |
| 8 | 12.0 | 16.5 |
| 9 | 12.9 | 2.5 |
| 10 | 15.3 | 18.7 |
| 11 | 16.6 | 5.5 |
| 12 | 16.9 | 7.0 |
| 13 | 17.8 | 30.0 |
| 14 | 18.1 | 9.4 |
| 15 | 18.5 | 15.5 |
| 16 | 19.1 | 9.9 |
| 17 | 19.8 | 25.4 |
| 18 | 20.4 | 18.1 |
| 19 | 20.7 | 14.1 |
| 20 | 21.3 | 5.8 |
| 21 | 21.7 | 5.6 |
| 22 | 22.4 | 5.1 |
| 23 | 22.8 | 41.9 |
| 24 | 23.1 | 17.7 |
| 25 | 24.2 | 42.1 |
| 26 | 24.7 | 19.7 |
| 27 | 25.0 | 26.6 |
| 28 | 25.4 | 3.7 |
| 29 | 25.9 | 8.7 |
| 30 | 26.3 | 35.2 |
| 31 | 28.0 | 8.3 |
| 32 | 28.6 | 10.9 |
| 33 | 29.3 | 4.4 |
| 34 | 30.4 | 7.2 |
| 35 | 33.2 | 3.5 |

In an embodiment, the X-ray powder diffraction pattern of the crystal form C of the maleate of the compound of formula I is substantially shown in FIG. 1.

The crystal form C can also be characterized by DSC, with initial temperature of 97.0° C.±5° C. and peak temperature of 106.0° C.±5° C.

In an embodiment, in crystal form C, the molar ratio of the compound of formula I to maleic acid is 1:1~3, preferably 1:2.

Provided is also a process for preparing the crystal form C according the invention, comprising precipitating the maleate of the compound of formula I from a solvent.

In an embodiment, the process comprises the following steps:
1) dissolving the compound of formula I in a solvent, which is preferably heated to promote dissolution;
2) adding maleic acid; and
3) cooling for crystallization, filtering, washing and drying to obtain the crystal form C.

In step 1), the solvent is selected from the group consisting of methanol, ethanol, propanol, isopropanol, n-butanol, isobutanol, tertiary butanol, acetone, ethyl acetate and mixed solvent thereof; preferably ethanol.

In step 1), the amount of solvent added per 1 mol of the compound of formula I is 0.2 to 8 L, preferably 0.3 to 4 L, more preferably 0.5 to 2 L, most preferably 1 L.

In step 1), the heating temperature may be 40° C. to 90° C., preferably 50° C. to 80° C., more preferably 70° C. to 80° C.

In step 2), the amount of maleic acid added per 1 mol of the compound of formula I is 1.0 to 4.0 mol, preferably 1.6 to 3.0 mol, more preferably 2.0 to 2.4 mol, most preferably 2.2 mol.

Provided is also a crystalline composition comprising the crystal form C. In an embodiment, based on the weight of the crystalline composition, the content of crystal form C is 50% or more, preferably 80% or more, more preferably 90% or more, and most preferably 95% or more. The crystalline composition, in addition to the crystal form C, can also comprise the compound of formula I or salt thereof in other crystal or amorphous forms, or impurities other than these substances.

Crystal Form D

Provided is crystal form D of the maleate of the compound of formula I, which has diffraction peaks at 2θ=5.1°±0.2°, 9.5°±0.2°, 11.2°±0.2°, 17.6°±0.2°, 20.2°±0.2°, 23.0°±0.2° in X-ray diffraction (XRPD) pattern.

In a specific embodiment, the crystal form D has diffraction peaks at 2θ=5.1°±0.2°, 9.5°±0.2°, 11.2°±0.2°, 17.6°±0.2°, 20.2°±0.2°, 20.7°±0.2°, 23.0°±0.2°, 23.7°±0.2° in X-ray diffraction (XRPD) pattern.

In a more specific embodiment, the crystal form D has diffraction peak at 2θ=5.1°±0.2°, 5.6°±0.2°, 9.5°±0.2°, 11.2°±0.2°, 16.9°±0.2°, 17.6°±0.2°, 20.2°±0.2°, 20.7°±0.2°, 22.6°±0.2°, 23.0°±0.2°, 23.7°±0.2°, 24.5°±0.2° in X-ray diffraction (XRPD) pattern.

In a particular embodiment, the diffraction peaks of the crystal form D of the maleate of the compound of formula I are characterized as follows:

| Number | 2θ ± 0.2 (°) | Relative intensity (%) |
|---|---|---|
| 1 | 5.1 | 100.0 |
| 2 | 5.6 | 11.5 |
| 3 | 7.0 | 2.7 |
| 4 | 8.7 | 2.6 |
| 5 | 9.5 | 36.2 |
| 6 | 10.3 | 3.1 |
| 7 | 11.2 | 23.5 |
| 8 | 12.0 | 3.1 |
| 9 | 14.2 | 2.5 |
| 10 | 16.2 | 4.2 |
| 11 | 16.9 | 11.2 |
| 12 | 17.6 | 33.6 |
| 13 | 18.3 | 4.7 |
| 14 | 18.8 | 2.0 |
| 15 | 19.2 | 5.3 |
| 16 | 19.6 | 4.4 |
| 17 | 20.2 | 35.6 |
| 18 | 20.7 | 19.0 |
| 19 | 21.4 | 3.5 |
| 20 | 22.6 | 12.3 |
| 21 | 23.0 | 20.1 |
| 22 | 23.7 | 17.7 |
| 23 | 24.5 | 14.8 |
| 24 | 26.4 | 6.1 |
| 25 | 27.1 | 3.1 |
| 26 | 27.7 | 3.3 |
| 27 | 28.4 | 5.2 |
| 28 | 28.8 | 8.7 |
| 29 | 30.7 | 3.8 |

Figure 2:
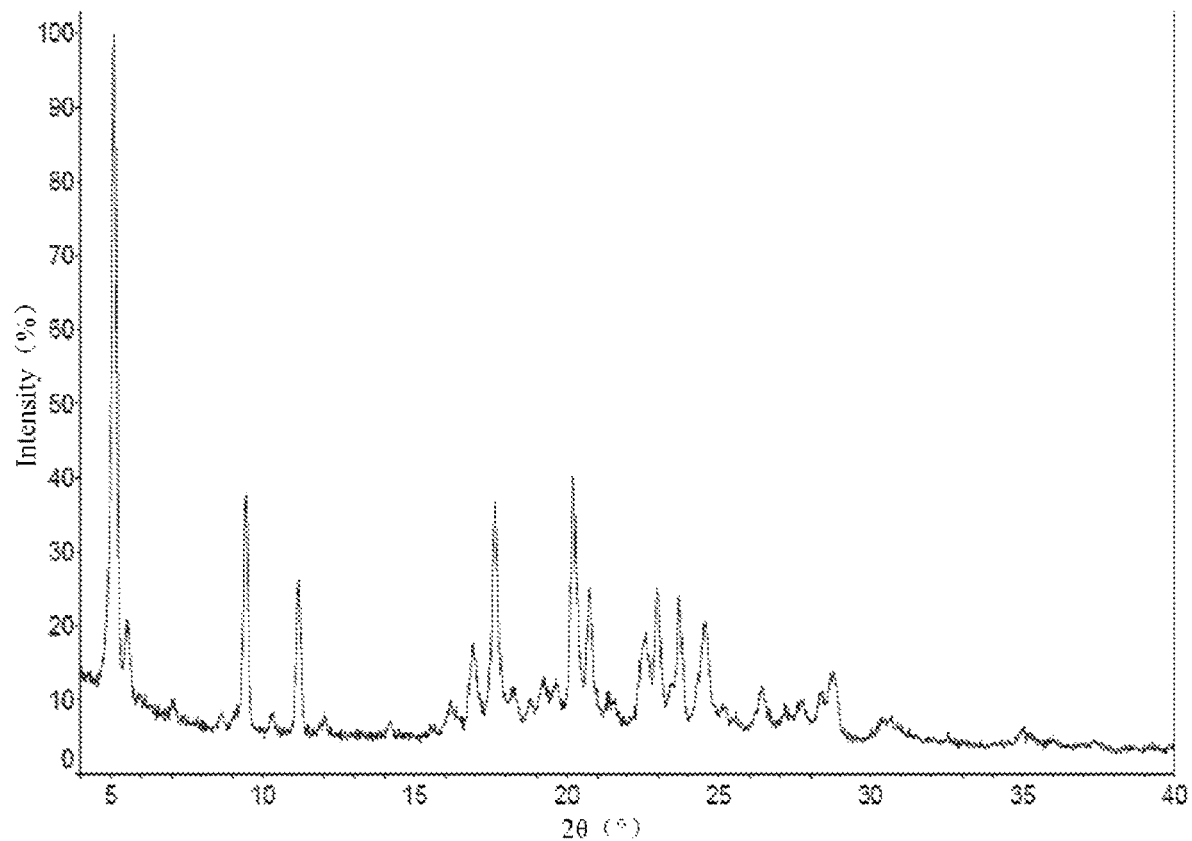
FIG. 2: XRPD pattern of the crystal form D of the maleate of the compound of formula I.

In an embodiment, the X-ray powder diffraction pattern of the crystal form D of the maleate of the compound of formula I is substantially shown in FIG. 2.

The crystal form D can also be characterized by DSC, with initial temperature of 98.3° C.±5° C. and peak temperature of 110.1° C.±5° C.

In an embodiment, in crystal form D the molar ratio of the compound of formula I to maleic acid is 1:1~3, preferably 1:2.

Provided is also a process for preparing the crystal form D, comprising the following steps:
1) placing the crystal form C of the maleate of the compound of formula I in acetone solvent to form a suspension;
2) shaking at constant temperature;
3) centrifugating, washing and drying to obtain the crystal form D.

In step 1), the amount of acetone added per 1 g of crystal form C of the maleate of the compound of formula I is 2 to 30 mL, preferably 8 to 24 mL, more preferably 12 to 20 mL, most preferably 14 to 16 mL.

In step 2), the constant temperature is 20° C. to 60° C., preferably 30° C. to 50° C., more preferably 35° C. to 45° C., most preferably 40° C.

Provided is also a crystalline composition comprising the crystal form D. In an embodiment, based on the weight of the crystalline composition, the crystal form D is 50% or more, preferably 80% or more, more preferably 90% or more, and most preferably 95% or more. Furthermore, the crystalline composition, in addition to the crystal form D, can also comprise compound of formula I or salt thereof in other crystal or amorphous forms, or impurities other than these substances.

Crystal Form E

Provided is crystal form E of the maleate of the compound of formula I, which has diffraction peaks at 2θ=4.9°±0.2°, 5.3°±0.2°, 9.0°±0.2°, 16.5°±0.2°, 19.3°±0.2° in X-ray diffraction (XRPD) pattern.

In a specific embodiment, the crystal form E has diffraction peaks at 2θ=4.9°±0.2°, 5.3°±0.2°, 6.7°±0.2°, 9.0°±0.2°, 10.8°±0.2°, 16.5°±0.2°, 19.3°±0.2° in X-ray diffraction (XRPD) pattern.

In a more specific embodiment, the crystal form E has diffraction peaks at 2θ=4.9°±0.2°, 5.3°±0.2°, 6.7°±0.2°, 9.0°±0.2°, 10.8°±0.2°, 16.2°±0.2°, 16.5°±0.2°, 19.3°±0.2°, 22.0°±0.2°, 22.6°±0.2°, 25.9°±0.2° in X-ray diffraction (XRPD) pattern.

In a specific embodiment, the diffraction peaks of the crystal form E of the maleate of the compound of formula I are characterized as follows:

| Number | 2θ ± 0.2 (°) | Relative intensity (%) |
|---|---|---|
| 1 | 4.9 | 100.0 |
| 2 | 5.3 | 10.4 |
| 3 | 6.7 | 6.9 |
| 4 | 8.2 | 2.8 |
| 5 | 8.6 | 2.7 |
| 6 | 9.0 | 7.9 |
| 7 | 10.8 | 5.1 |

-continued

| Number | 2θ ± 0.2 (°) | Relative intensity (%) |
|---|---|---|
| 8 | 16.2 | 3.9 |
| 9 | 16.5 | 15.4 |
| 10 | 17.7 | 2.0 |
| 11 | 19.3 | 7.2 |
| 12 | 22.0 | 4.6 |
| 13 | 22.6 | 4.0 |
| 14 | 24.3 | 2.3 |
| 15 | 25.9 | 3.4 |
| 16 | 27.1 | 2.8 |

Figure 3:
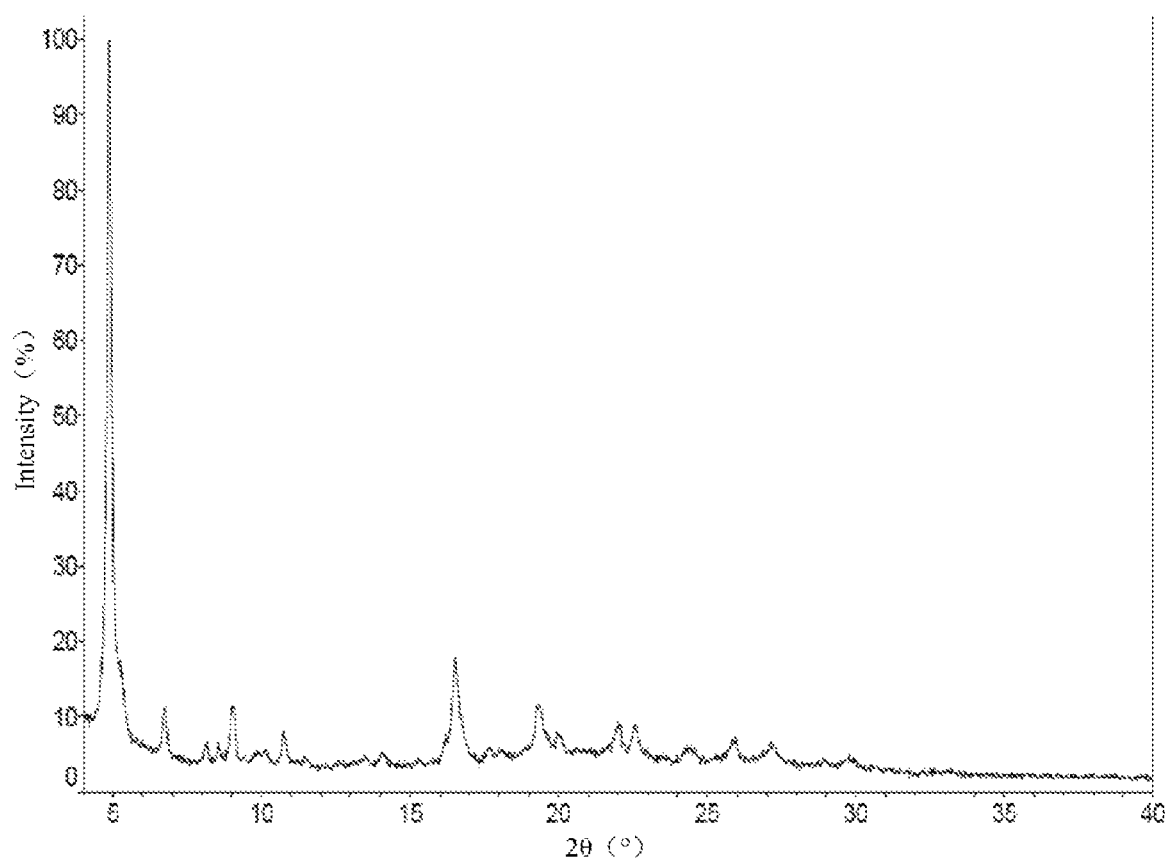
FIG. 3: XRPD pattern of the crystal form E of the maleate of the compound of formula I.

In an embodiment, the X-ray powder diffraction pattern of the crystal form E of the maleate of the compound of formula I is substantially shown in FIG. 3.

The crystal form E can also be characterized by DSC with initial temperature of 85.7° C.±5° C. and peak temperature of 97.5° C.±5° C.

In an embodiment, in crystal form E, the molar ratio of the compound of formula I to maleic acid is 1:1~3, preferably 1:2.

Provided is also a process for preparing the crystal form E, comprising the following steps:
1) placing the crystal form C of the maleate of the compound of formula I in isopropanol solvent to form a suspension;
2) shaking at constant temperature;
3) centrifugating, washing and drying to obtain the crystal form E.

In step 1), the amount of isopropanol added per 1 g of the crystal form C of the maleate of the compound of formula I is 2 to 30 mL, preferably 8 to 24 mL, more preferably 12 to 20 mL, further preferably 14 to 16 mL.

In step 2), the constant temperature is 20° C. to 60° C., preferably 30° C. to 50° C., more preferably 35° C. to 45° C., further preferably 40° C.

Provided is also a crystalline composition comprising the crystal form E. In an embodiment, based on the weight of the crystalline composition, crystal form E is 50% or more, preferably 80% or more, more preferably 90% or more, and most preferably 95% or more. The crystalline composition, in addition to crystal form E, can also comprise the compound of formula I or salt thereof in other crystal or amorphous forms, or impurities other than these substances.

Pharmaceutical Composition and Administration

Provided is a pharmaceutical composition, which comprises maleate of the compound of formula I; the crystal form C or the crystalline composition comprising the crystal form C; the crystal form D or the crystalline composition comprising the crystal form D; or the crystal form E or the crystalline composition comprising the crystal form E, or any combination thereof in an effective amount. Furthermore, the pharmaceutical composition also may or may not comprise pharmaceutically acceptable carrier, excipient and/or medium.

The compound according to the invention is administrated in a pure form or in a suitable pharmaceutical composition form, which can be performed via any acceptable administration mode of the agent with similar use. Pharmaceutical composition according to the invention may be prepared by combining of the compound according to the invention or the salt thereof with a suitable pharmaceutically acceptable carrier, for example it may be formulated into solid, semi-solid, liquid or gas formulation, such as tablet, pill, capsule, powder, granule, ointment, emulsion, suspension, solution, suppository, injection, inhalant, gel, microsphere, aerosol or the like.

The pharmaceutical composition according to the invention may be prepared by the processes well-known in the art, such as conventional mixing, dissolution, granulation, dragee coating, levigation, emulsion, freeze-drying or the like.

Typical routes for administering the compound according to the invention or the pharmaceutical composition thereof comprise but not limited to oral, rectal, transmucosal, enteral administration or local, transcutaneous, inhalant, parenteral, sublingual, intravaginal, intranasal, intraocular, intraperitoneal, intramuscular, subcutaneous, intravenous administration.

In a preferred embodiment, the pharmaceutical composition is in an oral administration form. As for oral administration, the active compounds may be mixed with the pharmaceutically acceptable carriers, excipients and/or media well-known in the art to prepare the pharmaceutical composition. The carriers, excipients and media may be used to prepare the compounds according to the invention into tablet, pill, troche, dragee, capsule, liquid, gel, slurry, suspension or the like useful for oral administration to the patient.

Solid oral composition may be prepared by conventional mixing, filling or compressing processes, for example, by the following processes: mixing the active compound with solid excipients, optionally milling the resultant mixture, adding other proper adjuvants if necessary, and then processing the mixture into granules so as to obtain the core of tablet or dragee. The proper excipients comprise but not limited to filler, such as sugar, including lactose, sucrose, mannitol or sorbitol; cellulose preparation such as microcrystalline cellulose, maize starch, wheat starch, rice starch and potato starch; and other substances, such as silica gel, gelatin, tragacanth, methylcellulose, hydroxypropylmethyl cellulose, carboxymethyl cellulose sodium and/or polyvinylpyrrolidone; disintegrant, such as carboxymethyl starch sodium, croscarmellose sodium, crosslinked polyvinylpyrrolidone, agar or alginic acid. Salt such as sodium alginate may also be used. The core of the dragee may be optionally coated through well-known processes in general pharmaceutical practice, especially by enteric coating.

Beneficial Effects

The crystal form C, crystal form D and crystal form E of the maleate of the compound of formula I according to the invention have the advantages of high purity, high crystallinity and good stability, which are suitable for the manufacture of a medicament for preventing or treating Toll-like receptor 7 (TLR7) associated disease.

The technical solutions of the invention are illustrated according to the following paragraphs [1] to [44]:

[1] A maleate of the compound of formula I,

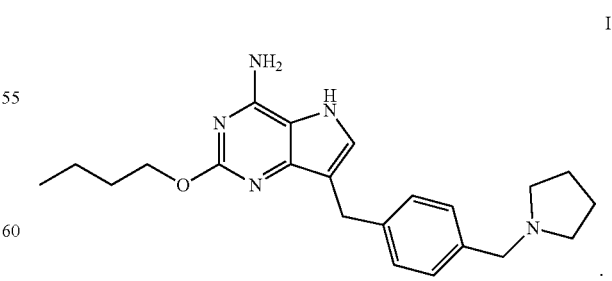

I

[2] The maleate of the compound of formula I according to paragraph [1], characterized in that, the molar ratio of the compound of formula I to the maleic acid is 1:1~3, preferably 1:2.

[3] A pharmaceutical composition, comprising the maleate of the compound of formula I according to paragraph [1] or [2] in an effective amount.

[4] Use of the maleate of the compound of formula I according to paragraph [1] or [2] or the pharmaceutical composition according to paragraph [3] for the manufacture of a medicament for treating toll-like receptor 7 associated disease.

[5] The use according to paragraph [4], characterized in that, the disease is virus infection, particularly hepatitis virus infection, for example hepatitis B or hepatitis C virus infection.

[6] A crystal form C of the maleate of the compound of formula I, characterized in that it has diffraction peaks at 2θ=7.6°±0.2°, 9.9°±0.2°, 17.8°±0.2°, 22.8°±0.2°, 24.2°±0.2°, 26.3°±0.2° in X-ray powder diffraction pattern.

[7] The crystal form C according to paragraph [6], characterized in that it has diffraction peaks at 2θ=5.6°±0.2°, 7.6°±0.2°, 9.9°±0.2°, 17.8°±0.2°, 19.8°±0.2°, 22.8°±0.2°, 24.2°±0.2°, 25.0°±0.2°, 26.3°±0.2° in X-ray powder diffraction pattern.

[8] The crystal form C according to paragraph [7], characterized in that it has diffraction peaks at 2θ=5.6°±0.2°, 6.0°±0.2°, 7.6°±0.2°, 9.9°±0.2°, 12.0°±0.2°, 15.3°±0.2°, 17.8°±0.2°, 18.5°±0.2°, 19.8°±0.2°, 20.4°±0.2°, 22.8°±0.2°, 23.1°±0.2°, 24.2°±0.2°, 24.7°±0.2°, 25.0°±0.2°, 26.3°±0.20 in X-ray powder diffraction pattern.

[9] The crystal form C according to any one of paragraphs [6]-[8], characterized in that, it has X-ray powder diffraction pattern substantially shown in FIG. 1.

[10] The crystal form C according to any one of paragraphs [6]-[9], characterized in that, when characterized by DSC, the initial temperature is 97.0° C.±5° C. and the peak temperature is 106.0° C.±5° C.

[11] A process for preparing the crystal form C according to any one of paragraphs [6]-[10], comprising the following steps:
1) dissolving the compound of formula I in a solvent, which is preferably heated to promote dissolution;
2) adding maleic acid;
3) cooling for crystallization, filtering, washing and drying to obtain the crystal form C.

[12] The preparing process according to paragraph [11], characterized in that the solvent in step 1) is selected from the group consisting of methanol, ethanol, propanol, isopropanol, n-butanol, isobutanol, tertiary butanol, acetone, ethyl acetate and mixed solvent thereof.

[13] The preparing process according to paragraph [12], characterized in that the solvent is ethanol.

[14] The preparing process according to any one of paragraphs [11]-[13], characterized in that, in step 1), the amount of solvent added per 1 mol of the compound of formula I is 0.2 to 8 L, preferably 0.3 to 4 L, more preferably 0.5 to 2 L, most preferably 1 L.

[15] The preparing process according to any one of paragraphs [11]-[14], characterized in that, in step 2), the amount of maleic acid added per 1 mol of the compound of formula I is 1.0 to 4.0 mol, preferably 1.6 to 3.0 mol, more preferably 2.0 to 2.4 mol, most preferably 2.2 mol.

[16] The preparation process according to any one of paragraphs [11]-[14], characterized in that, in step 1), the heating temperature may be 40° C. to 90° C., preferably 50° C. to 80° C., more preferably 70° C. to 80° C.

[17] A crystalline composition, characterized in that, based on the weight of the crystalline composition, the crystal form C according to any one of paragraphs [6]-[10] is 50% or more, preferably 80% or more, more preferably 90% or more, and most preferably 95% or more.

[18] A pharmaceutical composition, comprising the crystal form C according to any one of paragraphs [6]-[10] or the crystalline composition according to paragraph [17] in an effective amount.

[19] Use of the crystal form C according to any one of paragraphs [6]-[10] or the crystalline composition according to paragraph [17] or the pharmaceutical composition according to paragraph [18] for the manufacture of a medicament for treating Toll-like receptor 7 (TLR7) associated disease.

[20] The use according to paragraph [19], characterized in that the disease is virus infection, particularly hepatitis virus infection, such as hepatitis B or hepatitis C virus infection.

[21] A crystal form D of the maleate of the compound of formula I, characterized in that it has diffraction peaks at 2θ=5.1°±0.2°, 9.5°±0.2°, 11.2°±0.2°, 17.6°±0.2°, 20.2°±0.2°, 23.0°±0.2° in X-ray powder diffraction pattern.

[22] The crystal form D according to paragraph [21] characterized in that it has diffraction peaks at 2θ=5.1°±0.2°, 9.5°±0.2°, 11.2°±0.2°, 17.6°±0.2°, 20.2°±0.2°, 20.7°±0.2°, 23.0°±0.2°, 23.7°±0.2° in X-ray powder diffraction pattern.

[23] The crystal form D according to paragraph [22], characterized in that it has diffraction peaks at 2θ=5.1°±0.2°, 5.6°±0.2°, 9.5°±0.2°, 11.2°±0.2°, 16.9°±0.2°, 17.6°±0.2°, 20.2°±0.2°, 20.7°±0.2°, 22.6°±0.2°, 23.0°±0.2°, 23.7°±0.2°, 24.5°±0.2° in X-ray powder diffraction pattern.

[24] The crystal form D according to any one of paragraphs [21]-[23], characterized in that, the crystal form D has X-ray powder diffraction pattern substantially shown in FIG. 2.

[25] The crystal form D according to any one of paragraphs [21]-[24], characterized in that, when characterized by DSC, the initial temperature is 98.3° C.±5° C. and the peak temperature is 110.1° C.±5° C.

[26] A process for preparing the crystal form D according to paragraph [25], comprising the following steps:
1) placing the crystal form C of the maleate of the compound of formula I in acetone solvent to form a suspension;
2) shaking at constant temperature;
3) centrifugating, washing and drying to obtain the crystal form D.

[27] The preparing process according to any one of paragraphs [21]-[26], characterized in that, in step 1), the amount of acetone added per 1 g of crystal form C of the maleate of the compound of formula I is 2 to 30 mL, preferably 8 to 24 mL, more preferably 12 to 20 mL, most preferably 14 to 16 mL.

[28] The preparing process according to any one of paragraphs [21]-[27], characterized in that, in step 2), the constant temperature is 20° C. to 60° C., preferably 30° C. to 50° C., more preferably 35° C. to 45° C., most preferably 40° C.

[29] A crystalline composition, characterized in that, based on the weight of the crystalline composition, the crystal form D according to any one of paragraphs [21]-[25] is 50% or more, preferably 80% or more, more preferably 90% or more, and most preferably 95% or more.

[30] A pharmaceutical composition, comprising the crystal form D according to any one of paragraphs [21]-[25] or the crystalline composition according to paragraph [29] in an effective amount.

[31] Use of the crystal form D according to any one of paragraphs [21]-[25] or the crystalline composition according to paragraph [29] or the pharmaceutical composition according to paragraph [30] for the manufacture of a medicament for treating Toll-like receptor 7 (TLR7) associated disease.

[32] The use according to paragraph [31], characterized in that the disease is virus infection, particularly hepatitis virus infection, such as hepatitis B or hepatitis C virus infection.
[33] A crystal form E of the maleate of the compound of formula I characterized in that it has diffraction peaks at 2θ=4.9°±0.2°, 5.3°±0.2°, 9.0°±0.2°, 16.5°±0.2°, 19.3°±0.2° in X-ray powder diffraction pattern.
[34] The crystal form E according to paragraph [33] characterized in that it has diffraction peaks at 2θ=4.9°±0.2°, 5.3°±0.2°, 6.7°±0.2°, 9.0°±0.2°, 10.8°±0.2°, 16.5°±0.2°, 19.3°±0.2° in X-ray powder diffraction pattern.
[35] The crystal form E according to paragraph [34], characterized in that it has diffraction peaks at 2θ=4.9°±0.2°, 5.3°±0.2°, 6.7°±0.2°, 9.0°±0.2°, 10.8°±0.2°, 16.2°±0.2°, 16.5°±0.2°, 19.3°±0.2°, 22.0°±0.2°, 22.6°±0.2°, 25.9°±0.2° in X-ray powder diffraction pattern.
[36] The crystal form E according to any one of paragraphs [33]-[35], characterized in that, the crystal form E has X-ray powder diffraction pattern substantially shown in FIG. 3.
[37] The crystal form E according to any one of paragraphs [33]-[36], characterized in that, when characterized by DSC, the initial temperature is 85.7° C.±5° C. and the peak temperature is 97.5° C.±5° C.
[38] A process for preparing the crystal form E according to any one of paragraphs [33]-[37], comprising the following steps:
1) placing the crystal form C of the maleate of the compound of formula I in isopropanol solvent to form a suspension;
2) shaking at constant temperature;
3) centrifugating, washing and drying to obtain the crystal form E.
[39] The preparing process according to paragraph [38], characterized in that, in step 1), the amount of isopropanol added per 1 g of the crystal form C of the maleate of the compound of formula I is 2 to 30 mL, preferably 8 to 24 mL, more preferably 12 to 20 mL, further preferably 14 to 16 mL.
[40] The preparing process according to paragraphs [38] or [39], characterized in that, in step 2), the constant temperature is 20° C. to 60° C., preferably 30° C. to 50° C., more preferably 35° C. to 45° C., further preferably 40° C.
[41] A crystalline composition, characterized in that, based on the weight of the crystalline composition, the crystal form E according to any one of paragraphs [33]-[37] is 50% or more, preferably 80% or more, more preferably 90% or more, and most preferably 95% or more.
[42] A pharmaceutical composition, comprising the crystal form E according to any one of paragraphs [33]-[37] or the crystalline composition according to paragraph [41] in an effective amount.
[43] Use of the crystal form E according to any one of paragraphs [33]-[37] or the crystalline composition according to paragraph [41] or the pharmaceutical composition according to paragraph [42] for the manufacture of a medicament for treating Toll-like receptor 7 (TLR7) associated disease.
[44] The use according to paragraph [43], characterized in that the disease is virus infection, particularly hepatitis virus infection, such as hepatitis B or hepatitis C virus infection.

EXAMPLES

The following abbreviations are used herein: SEM-Cl: 2-(trimethylsilyl)ethoxymethyl chloride; SEM: 2-(trimethylsilyl)ethoxymethyl; DIPEA: diisopropylethylamine; TFA: trifluoroacetic acid; DMF: N,N-dimethylformamide; n-BuOH: n-butanol; $NH_3 \cdot H_2O$: aqueous ammonia; Na: sodium; XRPD: X-ray powder diffraction; DSC: differential thermal analysis.

In the present invention, X-ray diffraction pattern was determined as follows: apparatus: Bruker D8 ADVANCE X-ray diffractometer; method: target: Cu: K-Alpha; wavelength λ=1.54179 Å; voltage: 40 kV; current: 40 mA; scanning range: 4~40°; sample rotation speed: 15 rpm; scanning speed: 10°/min.

The solvents used herein are commercially available and can be used without further purification. The synthesis reactions in preparation examples are generally performed under inert nitrogen atmosphere in anhydrous solvent. Data of proton magnetic resonance is recorded in Bruker Avance III 400 (400 MHz) spectrometer, with the chemical shift shown as (ppm) at tetramethylsilane low field. Mass spectrometry is determined on Agilent 1200 plus 6110 (&1956A). LC/MS or Shimadzu MS includes a DAD: SPD-M20A(LC) and Shimadzu Micromass 2020 detector. Mass spectrometer is equipped with an electrospray ionization (ESI) operated at positive or negative mode.

Preparation Example 1: Preparation of 2-butoxy-7-(4-(pyrrolidin-1-ylmethyl)benzyl)-5H-pyrrolo[3,2-d]pyrimidin-4-amine maleate Formula III: 2,4-dichloro-5-((2-(trimethylsilyl)ethoxy)methyl)-5H-pyrrolo[3,2-d]pyrimidine

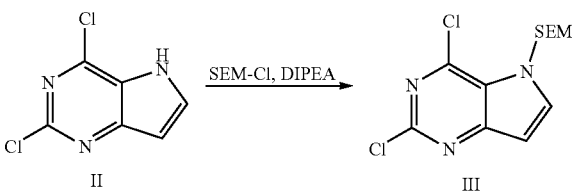

The compound of formula II (2,4-dichloro-5H-pyrrolo[3,2-d]pyrimidine) (4.00 kg, 21.28 mol) was dissolved in DMF (20.00 L), and DIPEA (2.58 kg, 20.00 mol) was added in portions at room temperature (25° C.) followed by stirring for 30 min. The reaction liquid was cooled to 0° C. with an ice bath, and then SEM-Cl (4.00 kg, 24.00 mol) was added dropwise slowly over 5 h at a dropping rate of 1 to 2 drops per second. After addition, the reaction liquid was stirred at 0° C. for 4 h. The reaction was monitored by HPLC. After completion, the reaction liquid was quenched and diluted with 70 L of water and then extracted with ethyl acetate (15 L×3). The combined organic phase was washed successively with 1 M aqueous hydrochloric acid (5 L×2) and saturated brine (7 L×2), and the solvent was removed by distillation under reduced pressure to give the compound of formula III (6.40 kg, 20.11 mol, yield 94.50%).

$^1$H NMR (400 MHz, DMSO-$d_6$) δ 8.24-8.35 (m, 1H), 6.70-6.85 (m, 1H), 5.77 (s, 2H), 3.45-3.57 (m, 2H), 0.74-0.86 (m, 2H), 0.00 (s, 9H).

Formula IV: 2-chloro-5-((2-(trimethylsilyl)ethoxy)methyl)-5H-pyrrolo[3,2-d] pyrimidin-4-amine

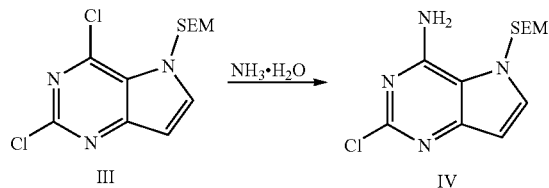

The compound of formula III (1.60 kg, 5.03 mol) was dissolved in isopropanol (1.60 L) in a 10 L clave. Aqueous ammonia (4 L) was added at room temperature (25° C.) in one portion and the reaction mixture was stirred at 95° C. for 7 h. The reaction was monitored by HPLC.

After completion, the reaction liquid was allowed to cool to room temperature and filtered through a Buchner funnel to give a dark brown solid. The solid was successively slurried with ethyl acetate/n-heptane (1/1, 5 L×2) and ethyl acetate (4 L) to give the compound of formula IV as brown solid (1.25 kg, 4.18 mol, yield 83.1%).

$^1$H NMR (400 MHz, DMSO-$d_6$) δ 7.61-7.77 (m, 1H), 6.97-7.19 (m, 2H), 6.28-6.38 (m, 1H), 5.54-5.67 (m, 2H), 3.43-3.53 (m, 2H), 0.76-0.91 (m, 2H), 0.07 (s, 9H).

Formula V: 2-butoxy-5-((2-(trimethylsilyl)ethoxy)methyl)-5H-pyrrolo[3,2-d]pyrimidin-4-amine

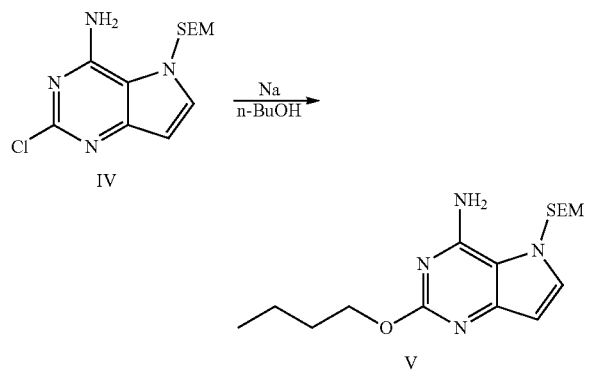

To n-BuOH (17.0 L) was slowly added metal sodium (525.05 g, 22.84 mol) in portions under nitrogen. After addition, the temperature of the system was raised to 60° C., and stirring was performed continuously at the temperature until the metal sodium was completely dissolved. Then the system was cooled to 25° C., and the compound of formula IV (1.95 kg, 6.53 mol) was added in portions. After being mixed homogenously with stirring, the reaction mixture was continuously stirred for 8 h at 90° C. The reaction was monitored by HPLC. After completion, the reaction mixture was allowed to cool spontaneously to 25° C., and slowly poured into 30 L of saturated aqueous ammonium chloride. Then the reaction mixture was extracted with ethyl acetate (15 L×3) and the combined organic phase was washed with saturated brine (20 L×2), dried with anhydrous $Na_2SO_4$, and filtered. After the solvent was distilled off under reduced pressure, the residue was slurried in n-heptane (4 L) and the solid was separated by filtration and slurried in ethyl acetate (5 L) to give the compound of formula V as yellow-white solid (1.53 kg, 4.55 mol, 69.7%).

$^1$H NMR (400 MHz, DMSO-$d_6$) δ 7.49-7.54 (m, 1H), 6.54-6.62 (m, 2H), 6.15-6.20 (m, 1H), 5.54 (s, 2H), 4.10-4.22 (m, 2H), 3.42-3.55 (m, 2H), 1.58-1.73 (m, 2H), 1.35-1.47 (m, 2H), 0.90-0.96 (m, 3H), 0.83-0.89 (m, 2H), 0.05 (s, 9H).

Formula VI: 2-butoxy-5H-pyrrolo[3,2-d]pyrimidin-4-amine

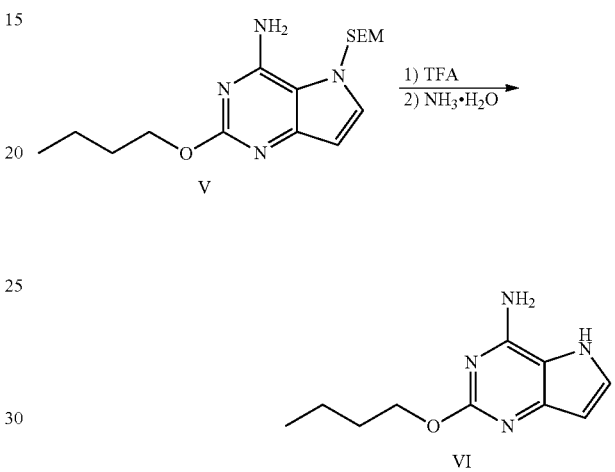

The compound of formula V (1.10 kg, 3.27 mol) was dissolved in TFA (5.50 L) and the reaction liquid was stirred at 25° C. for 16 h. The reaction was monitored by HPLC. After completion, TFA was removed by distillation under reduced pressure and the residue was dissolved in methanol (1.2 L) and ice water (1.2 L). pH of the system was adjusted to 12 with concentrated aqueous ammonia under uniform stirring. The mixture was stirred for 2 h and the precipitate was precipitated from the solution continuously. After filtration, the filter cake as white solid was slurried with 15% aqueous ammonia (1.2 L×3) and ethyl acetate (4 L) successively to give the compound of formula VI as white solid (550.00 g, 2.67 mol, 81.7%).

$^1$H NMR (400 MHz, methanol-$d_4$) δ 7.37 (d, J=2.89 Hz, 1H), 6.29 (d, J=3.01 Hz, 1H), 4.27 (t, J=6.53 Hz, 2H), 1.75 (d, J=7.91 Hz, 2H), 1.44-1.61 (m, 2H), 1.00 (t, J=7.40 Hz, 3H).

Formula VII: 4-((4-amino-2-butoxy-5H-pyrrolo[3,2-d]pyrimidin-7-yl)-hydroxymethyl)benzaldehyde

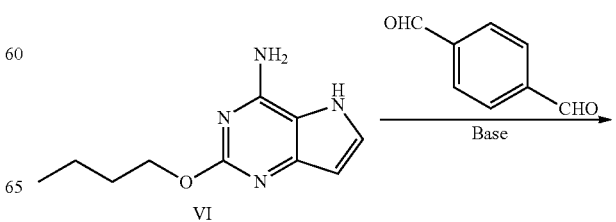

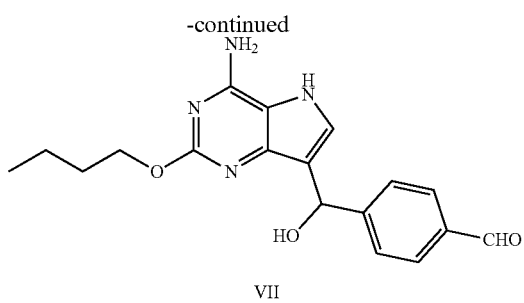

VII

To a three-necked flask were added terephthalaldehyde (790.64 mg, 5.82 mmol) and isopropanol (10 mL), 2-butoxy-5H-pyrrolo[3,2-d]pyrimidin-4-amine (1.00 g, 4.85 mmol) was added with stirring, and the system was cooled to 0° C. and stirred for another 10 min. Purified water (10 mL) and potassium carbonate (804.17 mg, 5.82 mmol) were added, and reacted at 25° C. for 16 h until the reactants were depleted with the monitor by LCMS. A solid was precipitated out after the reaction was completed. After filtration, the resulting solid was slurried with 20 mL of purified water and 30 mL (ethyl acetate/n-heptane=1/20) successively, filtered and dried to give the compound of formula VII as yellow solid (1.50 g, 4.41 mmol, yield: 90.9%).

$^1$H NMR (400 MHz, methanol-$d_4$) δ 9.94 (s, 1H), 7.86 (d, J=8.16 Hz, 2H), 7.72 (d, J=8.16 Hz, 2H), 7.12-7.17 (m, 1H), 6.19 (s, 1H), 4.28 (t, J=6.53 Hz, 2H), 1.68-1.77 (m, 2H), 1.44-1.54 (m, 2H), 0.97 (t, J=7.34 Hz, 3H).

Formula VIII: (4-amino-2-butoxy-5H-pyrrolo[3,2-d]pyrimidin-7-yl)(4-(pyrrolidin-1-ylmethyl)phenyl)methanol

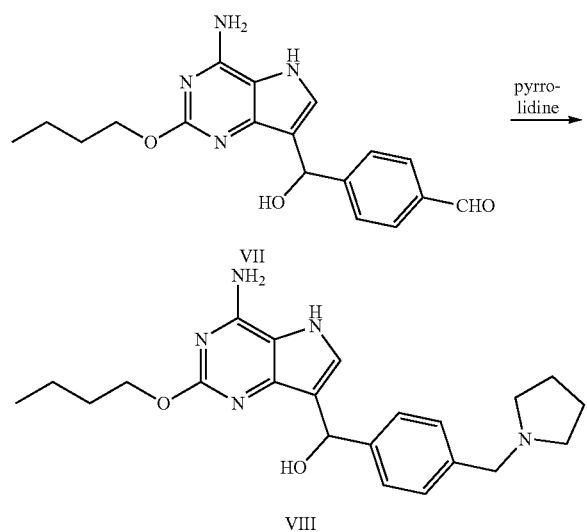

To a 30 L reactor were added the compound of formula VII (450.0 g, 1.32 mol) and isopropanol (4.5 L), and the mixture was stirred for 5 min. Then glacial acetic acid (119.0 g, 1.98 mol) was added and the temperature was lowered to 0-10° C. with stirring. Pyrrolidine (112.4 g, 1.58 mol) was added dropwise, with the temperature below 10° C. After addition, sodium triacetoxyborohydride (420.0 g, 1.98 mol) was added in portions and reacted at 10-20° C. for 3 h until the raw materials were depleted with the monitor by liquid chromatography. After the completion of the reaction, 5 L of purified water was added and the temperature of the solution was lowered to about −10° C., and 12 L of 15% aqueous ammonia was added to the solution, with the solution temperature below 0° C. during the addition. Solid was precipitated out under stirring. Filtration was performed and the resulting filter cake was slurried with 2 L of water and 2 L×2 ethyl acetate. Filtration was performed and drying was conducted under reduced pressure at 40° C. for 12 h to give the compound of formula VIII as yellow solid (465.0 g, 1.18 mol, yield 89.4%, moisture 0.9%).

$^1$H NMR (400 MHz, methanol-$d_4$) δ 7.46 (d, J=7.91 Hz, 1H), 7.29 (d, J=8.03 Hz, 1H), 7.09 (s, 1H), 6.12 (s, 1H), 4.29 (t, J=6.53 Hz, 2H), 3.60 (s, 2H), 2.52 (br. s., 4H), 1.66-1.83 (m, 6H), 1.49 (d, J=7.53 Hz, 2H), 0.98 (t, J=7.40 Hz, 3H).

Formula I: 2-butoxy-7-(4-(pyrrolidin-1-ylmethyl)benzyl)-5H-pyrrolo[3,2-d]pyrimidin-4-amine

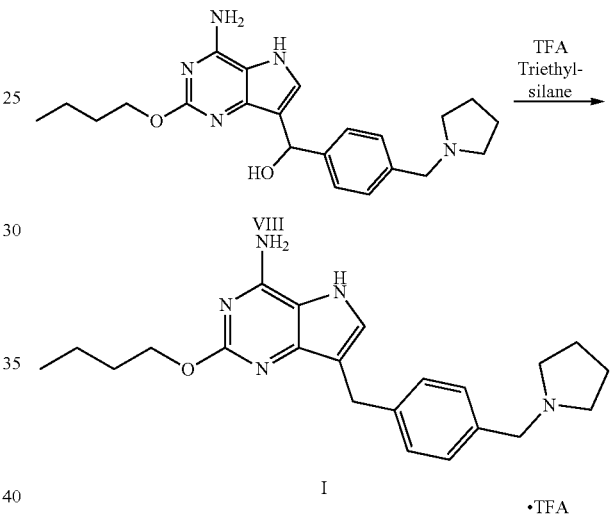

To 20 L clave were added the compound of formula VIII (440.0 g, 1.11 mol) and dichloromethane (7.0 L), and the temperature of the system was lowered to below −15° C. with stirring. After triethylsilane (880 mL, 5.55 mol) was added dropwise to the system, trifluoroacetic acid (880 mL) was added dropwise continuously, with the temperature kept below −10° C. during addition. After addition, the reaction was carried out at 0° C. for 2 h and monitored by liquid chromatography until the raw material point disappeared. After completion of the reaction, the reaction liquid was concentrated to dryness, and 2.2 L of ethyl acetate was added to the solution. Stirring was performed to lower the temperature to below 0° C. Then saturated sodium carbonate solution was added to adjust the solution to pH 9-10, during which the system temperature was kept below 10° C. Filtration was performed and the resulting filter cake was slurried with 2.2 L of water. Filtration was performed and drying was conducted under reduced pressure to give 550 g of trifluoroacetate of the compound of formula I as white solid.

To 1.6 L of ethanol was added 525 g of trifluoroacetate of the compound of formula I as white solid, and the temperature of the system was lowered to about 0° C. with stirring. Then 2.2 L of 1 mol/L sodium hydroxide solution was added. Filtration was performed and the resulting filter cake was slurried with 2.5 L of purified water. Filtration was performed and drying was conducted under reduced pressure to give 380.0 g of the compound of formula I as solid.

$^1$H NMR (400 MHz, methanol-$d_4$) δ 7.27 (d, J=8.0 Hz, 2H), 7.22 (d, J=8.0 Hz, 2H), 7.04 (s, 1H), 4.32 (t, J=6.6 Hz, 2H), 3.99 (s, 2H), 3.60 (s, 2H), 2.55-2.52 (m, 4H), 1.85-1.71 (m, 6H), 1.55-1.48 (m, 2H), 1.00 (t, J=7.4 Hz, 3H).

Example 1: Preparation of Crystal Form C of Maleate of 2-butoxy-7-(4-(pyrrolidin-1-ylmethyl) benzyl)-5H-pyrrolo[3,2-d]pyrimidin-4-amine To 10 mL ethanol was added the compound of formula I (3.80 g, 10 mmol), which was heated to be dissolved. Then maleic acid (2.55 g, 22 mmol) was added to the solution and stirring was performed with heating continuously until the solution was clear. The solution was then allowed to cool to room temperature and stand for 1-2 h. The precipitate was filtered and the solid was dried under reduced pressure with an oil pump to give crystal form C of maleate of the compound of formula I as solid. In the resulting maleate, the molar ratio of the compound of formula I to maleic acid was 1:2.

XRPD was measured as follows: apparatus: Bruker D8 ADVANCE X-ray diffractometer; method: target: Cu: K-Alpha; wavelength λ=1.54179 Å; voltage: 40 kV; current: 40 mA; scanning range: 4~40°; sample rotation speed: 15 rpm; scanning speed: 10°/min.

The obtained compound crystal had diffraction peaks substantially as shown in FIG. 1.

Example 2: Preparation of Crystal Form D of Maleate of 2-butoxy-7-(4-(pyrrolidin-1-ylmethyl) benzyl)-5H-pyrrolo[3,2-d]pyrimidin-4-amine To 0.8 mL acetone was added crystal form C of maleate of compound of formula I (50 mg) to form a suspension. The suspension sample was shaken on a thermostat (40° C.) for 2 days (in dark). The residual solid was centrifuged and dried in a vacuum oven at 40° C. overnight to give crystal form D of maleate of the compound of formula I as solid. In the resulting maleate, the molar ratio of the compound of formula I to maleic acid was 1:2.

XRPD was measured as follows: apparatus: Bruker D8 ADVANCE X-ray diffractometer; method: target: Cu: K-Alpha; wavelength λ=1.54179 Å; voltage: 40 kV; current: 40 mA; scanning range: 4~40°; sample rotation speed: 15 rpm; scanning speed: 10°/min.

The obtained compound crystal had diffraction peaks substantially as shown in FIG. 2.

Example 3: Preparation of Crystal Form E of Maleate of 2-butoxy-7-(4-(pyrrolidin-1-ylmethyl) benzyl)-5H-pyrrolo[3,2-d]pyrimidin-4-amine To 0.8 mL isopropanol was added crystal form C of maleate of compound of formula I (50 mg) to form a suspension. The suspension sample was shaken on a thermostat (40° C.) for 2 days (in dark). The residual solid was centrifuged and dried in a vacuum oven at 40° C. overnight to give crystal form E of maleate of the compound of formula I as solid. In the resulting maleate, the molar ratio of the compound of formula I to maleic acid was 1:2.

XRPD was measured as follows: apparatus: Bruker D8 ADVANCE X-ray diffractometer; method: target: Cu: K-Alpha; wavelength λ=1.54179 Å; voltage: 40 kV; current: 40 mA; scanning range: 4~40°; sample rotation speed: 15 rpm; scanning speed: 10°/min.

The obtained compound crystal had diffraction peaks substantially as shown in FIG. 3.

Example 4: High Temperature Stability Test

The crystal forms prepared in Examples 1-3 were tested in the accelerated test under high temperature conditions for stability in accordance with *Guidelines for the Stability Test of Pharmaceutical Ingredients and Pharmaceutical Preparations* (Chinese Pharmacopoeia 2010 Appendix XIXC).

The crystal forms C, D and E prepared in Examples 1-3 were placed in an open-clean container at 60° C., respectively. The samples were taken for test on day 10, day 20 and day 30, respectively. The results were compared with the initial test result on day 0.

Example 5: High Humidity Stability Test

The crystal forms prepared in Examples 1-3 were tested in the accelerated test under high humidity conditions for stability in accordance with *Guidelines for the Stability Test of Pharmaceutical Ingredients and Pharmaceutical Preparations* (Chinese Pharmacopoeia 2010 Appendix XIXC).

The crystal forms C, D and E prepared in Examples 1-3 were subjected to an accelerated test in a constant temperature and humidity vessel under the conditions of 40° C./75% humidity (open). The samples were taken for test on day 30, day 60 and day 90, respectively. The results were compared with the initial test result on day 0.

Example 6: Light Stability

The crystal forms prepared in Examples 1-3 under light conditions were tested for stability in accordance with *Guidelines for the Stability Test of Pharmaceutical Ingredients and Pharmaceutical Preparations* (Chinese Pharmacopoeia 2010 Appendix XIXC).

The crystal forms C, D and E prepared in Examples 1-3 were respectively placed in an illumination environment of 5000 Lx±500 Lx. The samples were taken on day 5, day 10 and day 30. The test results were compared with the initial test result on day 0.

Examples of Pharmacological Activity

Efficacy Example 1: Toll-Like Receptor 7 and Toll-Like Receptor 8 In Vitro Receptor Binding Activity Screen Reagents:
HEK-blue hTLR7 cell and HEK-blue hTLR8 cell (available from InvivoGen)
DMEM medium
heat inactivated fetal bovine serum
Anti Mycoplasma reagent Normocin
bleomycin
blasticidin The structure of GS-9620 and R848 used are as follows, wherein the preparation of GS-9620 could be referred to the process disclosed in US20100143301; R848 was commercially available from ABGENT (IMG-2208, specification: 0.5 mg).

Scheme

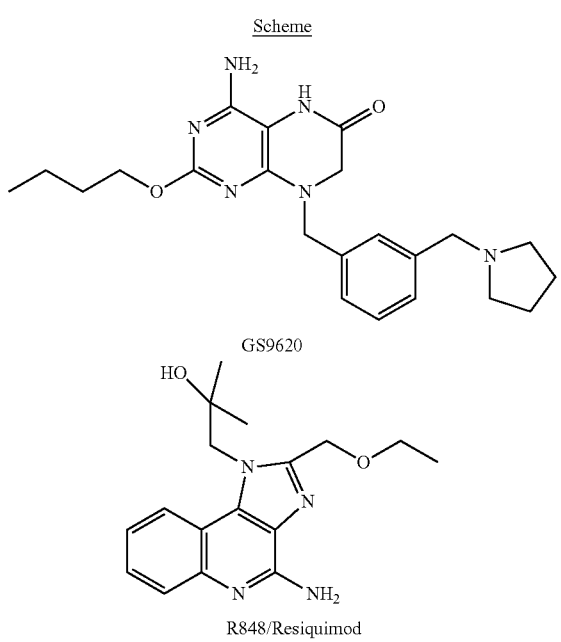

Scheme:
1. Preparation of 96-well compound plate:
The compounds were gradient diluted with DMSO in 3-fold using liquid work station POD starting at a concentration of 10 mmol/L and 10 points were diluted (2nd column to 11th column, and each point was duplicated). At 12th column, 1 μL of 5 mg/mL positive compound R848 was added as positive control; and at 1st column, 1 μL of DMSO was added as negative control. Each well contained 1 μL of DMSO.
2. The cells in culture flask were collected and the cell density was diluted to 250,000 cells/mL.
3. 200 μL (50,000 cells/well) of cell suspension was added into prepared compound plate and the final concentration of DMSO in each well was 0.5%.
4. The culture plates containing cells and the compounds were incubated in $CO_2$ incubator for 24 h at 37° C., 5% $CO_2$.
5. After 24 h incubation, 20 μL of supernatant was removed from each well to a 96-well transparent assay plate. To each well of the assay plate was added 180 μL of Quanti-Blue reagent and the plate was incubated in an incubator at 37° C., 5% $CO_2$ for 1 h.
6. After 1 h, the content of alkaline phosphatase in 20 μL of supernatant was determined using Microplate Reader OD650.
7. $EC_{50}$ of each compound was obtained with Prism software.
Results are shown in Table 1:

TABLE 1

| Name of the compound | TLR7 EC50 (nM) | TLR8 EC50 (nM) |
|---|---|---|
| GS-9620 | 517 | 7867 |
| The compound of formula I | 160 | 11632 |

As is shown in table 1, the compound of formula I according to the invention showed higher in vitro receptor binding activity to Toll-like receptor 7 than the control (Toll-like receptor 7 agonist GS-9620) and lower in vitro receptor binding activity to Toll-like receptor 8 than the control (Toll-like receptor 7 agonist GS-9620).

The compound of the present invention has distinct selectivity differences with respect to different receptors, and the effect is superior over the prior art.

Efficacy Example 2: Peripheral Blood Mononuclear Cell Test Scheme

The purpose of this example is to determine the expression level of cytokines 24 h after stimulation to human peripheral blood mononuclear cells (PBMC) with the compound of formula I.

The cell supernatant was assayed without dilution and the levels of IFN-α were directly determined. The compound of formula I was firstly formulated into 20 mM DMSO stock solution and was gradient diluted with cell medium in 10-fold with the total number of 11 diluting points. The compounds in 9 diluting points (the highest concentration was 200 μmol/L) were added into 96-well plate with 50 μL in each well. Fresh human peripheral blood mononuclear cells were inoculated, with 150 μL in each well containing 450,000 cells. The cell culture plate was incubated in an incubator at 37° C., 5% $CO_2$ for 24 h. After incubation, the culture plate was centrifuged at 1200 rpm for 5 min and the supernatant was collected and stored at −20° C. for determination. The determination of cytokine was performed using Cytometric Bead Array (CBA) of BD-Pharmingen on flow cytometer. Using the above determining method, the lowest drug concentration stimulating the production of 30 pg/mL of IFN-α was designated as the MEC value in the cytokine stimulating test. The results were shown in Table 2.

TABLE 2

| Name of the compound | IFN-α MEC (nM) | TNF-α MEC (nM) |
|---|---|---|
| GS-9620 | 50 | 500 |
| The compound of formula I | 5 | 500 |

Conclusion: Compared with the control (GS-9620), the compound of formula I of the invention showed better in vitro IFN-α inducing activity of PBMCs and comparable TNF-α inducing activity.

The invention claimed is:
1. A crystal form C of a maleate of a compound of formula I, wherein the crystal form C has diffraction peaks at 2θ=7.6°±0.2°, 9.9°±0.2°, 17.8°±0.2°, 22.8°±0.2°, 24.2°±0.2°, 26.3°±0.2° in X-ray powder diffraction pattern,

I

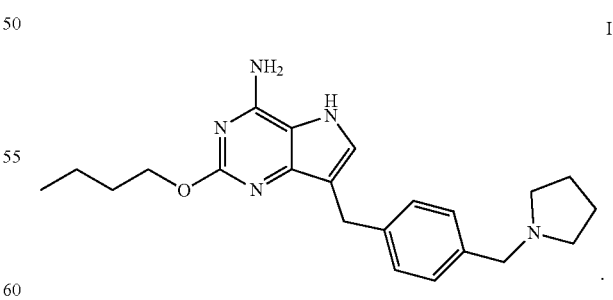

2. A process for preparing the crystal form C according to claim 1, comprising the following steps:
  1) dissolving the compound of formula I in a solvent;
  2) adding maleic acid; and
  3) cooling for crystallization, filtering, washing and drying to obtain the crystal form C, wherein the solvent is selected from the group consisting of methanol, ethanol, propanol, isopropanol, n-butanol, isobutanol, tertiary butanol, acetone, ethyl acetate and mixed solvent thereof.

3. A crystal form D of a maleate of a compound of formula I, wherein the crystal form D has diffraction peaks at 2θ=5.1°±0.2°, 9.5°±0.2°, 11.2°±0.2°, 17.6°±0.2°, 20.2°±0.2°, 23.0°±0.20 in X-ray powder diffraction pattern,

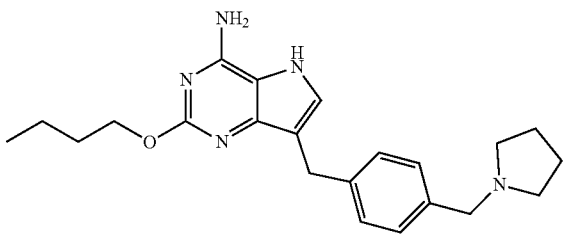

I

4. A process for preparing the crystal form D according to claim 3, comprising the following steps:
  1) placing a crystal form C of the maleate of the compound of formula I in acetone solvent to form a suspension;
  2) shaking at constant temperature; and
  3) centrifugating, washing and drying to obtain the crystal form D,
  wherein the crystal form C has diffraction peaks at 2θ=7.6°±0.2°, 9.9°±0.2°, 17.8°±0.2°, 22.8°±0.2°, 24.2°±0.2°, 26.3°±0.2° in X-ray powder diffraction pattern.

5. A crystal form E of a maleate of a compound of formula I, wherein the crystal form E has diffraction peaks at 2θ=4.9°±0.2°, 5.3°±0.2°, 9.0°±0.2°, 16.5°±0.2°, 19.3°±0.2° in X-ray powder diffraction pattern,

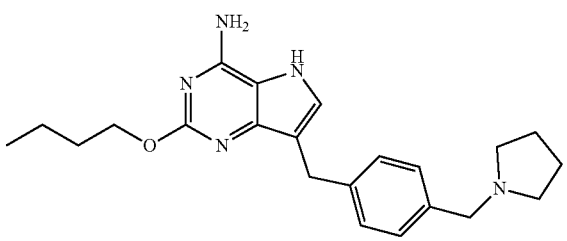

I

6. A process for preparing the crystal form E according to claim 5, comprising the following steps:
  1) placing a crystal form C of the maleate of the compound of formula I in isopropanol solvent to form a suspension;
  2) shaking at constant temperature; and
  3) centrifugating, washing and drying to obtain the crystal form E,
  wherein the crystal form C has diffraction peaks at 2θ=7.6°±0.2°, 9.9°±0.2°, 17.8°±0.2°, 22.8°±0.2°, 24.2°±0.2°, 26.3°±0.2° in X-ray powder diffraction pattern.

7. A pharmaceutical composition comprising the crystal form C according to claim 1 in an effective amount.

8. A pharmaceutical composition comprising the crystal form D according to claim 3 in an effective amount.

9. A pharmaceutical composition comprising the crystal form E according to claim 5 in an effective amount.

10. A method for treating hepatitis B viral infection or hepatitis C viral infection comprising administering a subject in need thereof the crystal form C according to claim 1.

11. A method for treating hepatitis B viral infection or hepatitis C viral infection comprising administering a subject in need thereof the crystal form D according to claim 3.

12. A method for treating hepatitis B viral infection or hepatitis C viral infection comprising administering a subject in need thereof the crystal form E according to claim 5.

13. A method for treating hepatitis B viral infection or hepatitis C viral infection comprising administering a subject in need thereof the pharmaceutical composition according to claim 7.

14. A method for treating hepatitis B viral infection or hepatitis C viral infection comprising administering a subject in need thereof the pharmaceutical composition according to claim 8.

15. A method for treating hepatitis B viral infection or hepatitis C viral infection comprising administering a subject in need thereof the pharmaceutical composition according to claim 9.

16. The process according to claim 2, wherein the solvent is ethanol.

* * * * *